（12）United States Patent
Pullen et al.

(10) Patent No.: US 9,585,383 B2
(45) Date of Patent: Mar. 7, 2017

(54) METHODS OF REDUCING PHYTOTOXICITY OF A PESTICIDE

(75) Inventors: Erroll M. Pullen, Somerset West (ZA); Dirk C. Uys, Somerset West (ZA)

(73) Assignee: ORO Agri, Inc., Trophy Club, TX (US)

( * ) Notice: Subject to any disclaimer, the term of this patent is extended or adjusted under 35 U.S.C. 154(b) by 250 days.

(21) Appl. No.: 13/214,517

(22) Filed: Aug. 22, 2011

(65) Prior Publication Data

US 2012/0046168 A1 Feb. 23, 2012

Related U.S. Application Data

(60) Provisional application No. 61/375,595, filed on Aug. 20, 2010.

(51) Int. Cl.
| | | |
|---|---|---|
| *A01N 25/30* | (2006.01) | |
| *A01N 25/32* | (2006.01) | |
| *A01N 65/36* | (2009.01) | |
| *A01N 25/06* | (2006.01) | |
| *C05G 3/06* | (2006.01) | |
| *C05C 9/00* | (2006.01) | |

(52) U.S. Cl.
CPC ............. *A01N 25/06* (2013.01); *A01N 25/30* (2013.01); *A01N 25/32* (2013.01); *A01N 65/36* (2013.01); *C05C 9/00* (2013.01); *C05G 3/06* (2013.01)

(58) Field of Classification Search
CPC ........ A01N 25/06; A01N 25/32; A01N 65/36; A01N 25/30; C05G 3/06; C05C 9/00
USPC .................................................. 504/206, 101
See application file for complete search history.

(56) References Cited

U.S. PATENT DOCUMENTS

| | | |
|---|---|---|
| 3,584,119 A | 6/1971 | Langley |
| 4,039,588 A | 8/1977 | Wilson et al. |
| 4,049,828 A | 9/1977 | Cole |
| 4,379,168 A | 4/1983 | Dotolo |
| 4,610,881 A | 9/1986 | Bechgaard |
| 4,978,686 A | 12/1990 | Sotome |
| 5,087,353 A | 2/1992 | Todd et al. |
| 5,110,804 A | 5/1992 | Lee |
| 5,118,506 A | 6/1992 | Eichofer |
| 5,143,939 A | 9/1992 | Browning |
| 5,330,671 A | 7/1994 | Pullen et al. |
| 5,374,600 A | 12/1994 | Hozumi et al. |
| 5,389,257 A | 2/1995 | Todd et al. |
| 5,444,078 A | 8/1995 | Yu et al. |
| 5,527,482 A | 6/1996 | Pullen et al. |
| 5,641,847 A | 6/1997 | Hozumi et al. |
| 5,679,351 A | 10/1997 | Walter et al. |
| 5,693,344 A | 12/1997 | Knight et al. |
| 5,744,137 A | 4/1998 | Stone |
| 5,753,593 A | 5/1998 | Pullen et al. |
| 5,863,456 A | 1/1999 | Pullen |
| 5,871,765 A | 2/1999 | Johnson et al. |
| 5,876,622 A | 3/1999 | Pullen et al. |
| 5,885,600 A | 3/1999 | Blum et al. |
| 5,900,243 A | 5/1999 | Yoder et al. |
| 5,948,743 A | 9/1999 | Fonsny et al. |
| 5,958,287 A | 9/1999 | Pullen |
| 5,977,186 A | 11/1999 | Franklin |
| 6,093,856 A | 7/2000 | Cripe et al. |
| 6,124,366 A | 9/2000 | Pullen et al. |
| 6,130,253 A | 10/2000 | Franklin et al. |
| 6,248,710 B1 | 6/2001 | Bijsterbosch et al. |
| 6,251,951 B1 | 6/2001 | Emerson et al. |
| 6,258,369 B1 | 7/2001 | Pullen |
| 6,277,389 B1 | 8/2001 | Pullen |
| 6,455,086 B1 | 9/2002 | Trinh et al. |
| 6,500,445 B1 | 12/2002 | Pullen |
| 6,514,512 B1 | 2/2003 | Puterka et al. |
| 6,582,712 B2 | 6/2003 | Pullen |
| 6,689,342 B1 | 2/2004 | Pan et al. |
| 7,294,341 B2 | 11/2007 | Pullen |
| 7,341,735 B2 | 3/2008 | Pullen |
| 8,092,817 B2 | 1/2012 | Pullen et al. |
| 2003/0035852 A1 | 2/2003 | Pullen |
| 2003/0060379 A1 | 3/2003 | Souter et al. |
| 2003/0224939 A1 | 12/2003 | Miles |
| 2004/0138176 A1 | 7/2004 | Miles |
| 2004/0242428 A1 | 12/2004 | Pullen |
| 2008/0064603 A1 | 3/2008 | Pullen |
| 2008/0070787 A1 | 3/2008 | Pullen |

(Continued)

FOREIGN PATENT DOCUMENTS

| | | |
|---|---|---|
| EP | 0943239 A1 | 9/1999 |
| WO | 9639846 | 12/1996 |

(Continued)

OTHER PUBLICATIONS

Pesticide Application Equipment [online]. Floriculture Production Guide, 2008 [retrieved on Apr. 29, 2015]. Retrieved from the Internet<http://www.agf.gov.bc.ca/ornamentals/floriculture/floriculture_guide/chapter12.pdf>, pp. 1-6.*
Stonehouse, J.M., Studies of the Distribution of Ultra Low Volume Spray Applied Within a Crop Canopy, 1993, Journal of Agric. Engng. Res., vol. 54, pp. 201-210.*
Tripathi N. N. et al., "Toxicity of Some Terpenoids Against Fungi Infesting Fruits and Seeds of Capsicum-Annuum During Storate", Phytopatologische Zeitschrift, 1984, pp. 328-335, vol. 110, Vertag Paul Parey, Berlin, DE.
Bauske, et al., Management of Meloidogyne Incognita on Cotton by Use of Botanical Compounds, Nematropica 24: 142-150 (1994).
Chery Lin, Chemical Constituents of Essenntial Oils, Updated May 2007.

*Primary Examiner* — Mina Haghighatian
*Assistant Examiner* — Andriae M Holt
(74) *Attorney, Agent, or Firm* — Knobbe Martens Olson & Bear LLP

(57) ABSTRACT

The present invention provides novel methods of applying pesticides to control pests with reduced phytotoxicity effects. The method comprises applying pesticides as microdroplets in a low volume but high concentration.

24 Claims, 2 Drawing Sheets

(56) References Cited

U.S. PATENT DOCUMENTS

2008/0166437 A1    7/2008   Rosskopf et al.
2008/0214400 A1    9/2008   Pullen
2010/0144534 A1    6/2010   Pullen

FOREIGN PATENT DOCUMENTS

| WO | 9716975 | 5/1997 |
|---|---|---|
| WO | 9802044 | 1/1998 |
| WO | 0049865 A2 | 8/2000 |
| WO | 0113726 | 3/2001 |
| WO | 0126457 A2 | 4/2001 |
| WO | 03020024 | 3/2003 |
| WO | 03056917 A2 | 7/2003 |
| WO | 2005070213 A2 | 8/2005 |
| WO | 2006052228 | 5/2006 |
| WO | 2008097553 | 8/2008 |
| WO | 2011031287 | 3/2011 |

* cited by examiner

METHODS OF REDUCING PHYTOTOXICITY OF A PESTICIDE

This application claims priority to U.S. provisional application Ser. No. 61/375,595, filed Aug. 20, 2010, titled "Methods of Reducing Phytotoxicity of a Pesticide," the disclosure of which is incorporated herein in its entirety by reference thereto.

FIELD OF THE INVENTION

The present invention relates to methods of pesticide application to a plant or crop without the risk of causing phytotoxicity.

BACKGROUND

Environmentally safe methods for the control of plant pests using non-toxic agents represent ecologically sound alternatives to the use of synthetic chemical pesticides, insecticides, fungicides, miticides, adjuvants for crop-care chemicals and the like. Damage caused to the environment, including natural aquifers and animal and plant species due to runoff of these chemicals is an ecological problem faced by virtually every country in the world. This environmental damage leads to enormous difficulties reflected in, for example, increased health care costs and ecological harm. There is a significant unmet need for environmentally safe methods for the control of pests using agents having low, or no phytotoxicity, but which have high activity against target pests.

The need in the industry is for environmentally safe methods for the control of pests through, in the first instance, the efficient application of pesticides without resulting in phytotoxicity, and additionally by obtaining a complete coverage of the foliage and fruit. In the second instance, lower spray volumes save on refilling time of the spray tank, resulting in more spraying time compared to refilling time. This leads to more efficient use of equipment and fuel and operator time. It also saves on energy needs by either having less volume of spray solution to pressurize or in other instances, eliminating the need for air fans delivering huge volumes of high speed air flow.

SUMMARY OF THE INVENTION

The present inventors have discovered and disclose herein novel methods of applying pesticides for controlling pests with in a manner that no or very little phytotoxicity is caused. The present invention provides methods of applying pesticides to plants and/or crops comprising applying high concentration of pesticides at a low volume. In one embodiment, the methods of the present invention involve applying micro-droplets of pesticides to the plants and/or crops. The micro-droplets of pesticides may be formed using an electrostatic spray system or a fogger.

The present invention is directed to methods of applying pesticides to a plant or crop in a low volume spray at high concentration. The spray is typically in the form of micro-droplets of pesticides that may be applied to a plant or crop using any method including an electrostatic sprayer.

The pesticides used in the methods of the present application may be compositions comprising one or more surfactants and one or more high terpene containing oils. The composition may also include one or more salts of boric acid.

In certain embodiments, the compositions of the invention may comprise one or more surfactants selected from the group consisting of non-ionic, anionic, cationic, and amphoteric surfactants.

In certain embodiments, the compositions of the invention comprise one or higher terpene based oils. The high terpene based oil may be a citrus oil. The citrus oil may be selected from the group consisting of orange oil, lemon oil, lime oil, grapefruit oil, and tangerine oil.

In certain embodiments, the compositions of the invention comprise one or more surfactants which are a blend of one or more alcohols and one or more polysaccharides. The one or more surfactants may comprise one or more alkyl glucosides.

In certain embodiments, the compositions of the invention comprise one or more salts of boric acid selected from the group consisting of alkali metal salts of boric acid In certain embodiments, the compositions of the invention comprise one or more alkali metal salts of boric acid. The compositions of the invention may comprise a sodium salt of boric acid. The compositions of the invention may comprise borax.

In certain embodiments, the compositions of the invention comprise an alkyl glucoside, borax and orange oil. The alkyl glucoside may be a non-ionic surfactant.

In certain embodiments, the compositions of the invention further comprise one or more agents selected from the group consisting of insecticides, fungicides, miticides, herbicides, acaricides, fertilizers, nutrients, and plant growth regulators.

In certain embodiments, the invention is directed to methods of controlling pests on plants or crops including transgenic or non-transgenic plants comprising application of pesticidal composition by the methods of the claimed invention to any plant or crop to thereby control the pests.

In certain embodiments, the methods disclosed herein, involve obtaining micro-droplets of the pesticidal composition and applying it to the plant or crop.

The modes of application may be selected from the group consisting of spraying, wetting, misting, fogging, dampening and drizzling. The micro-droplets may be formed prior to or concurrently with applying the pesticidal composition to the plant.

In certain embodiments, the pests to be controlled are selected from the group consisting of insects, mites and fungi.

BRIEF DESCRIPTION OF THE DRAWINGS

FIG. 2A shows product at 234 L/ha water rate. FIG. 2B shows product at 140 L/ha water rate. Product at 140 L/ha water rate showed excellent coverage on top and bottom of leaf even at lower water rates with less runoff and still no phytotoxic effect even at higher concentration rates (same rates per hectare in lower water volumes).

DETAILED DESCRIPTION

Figure 1:
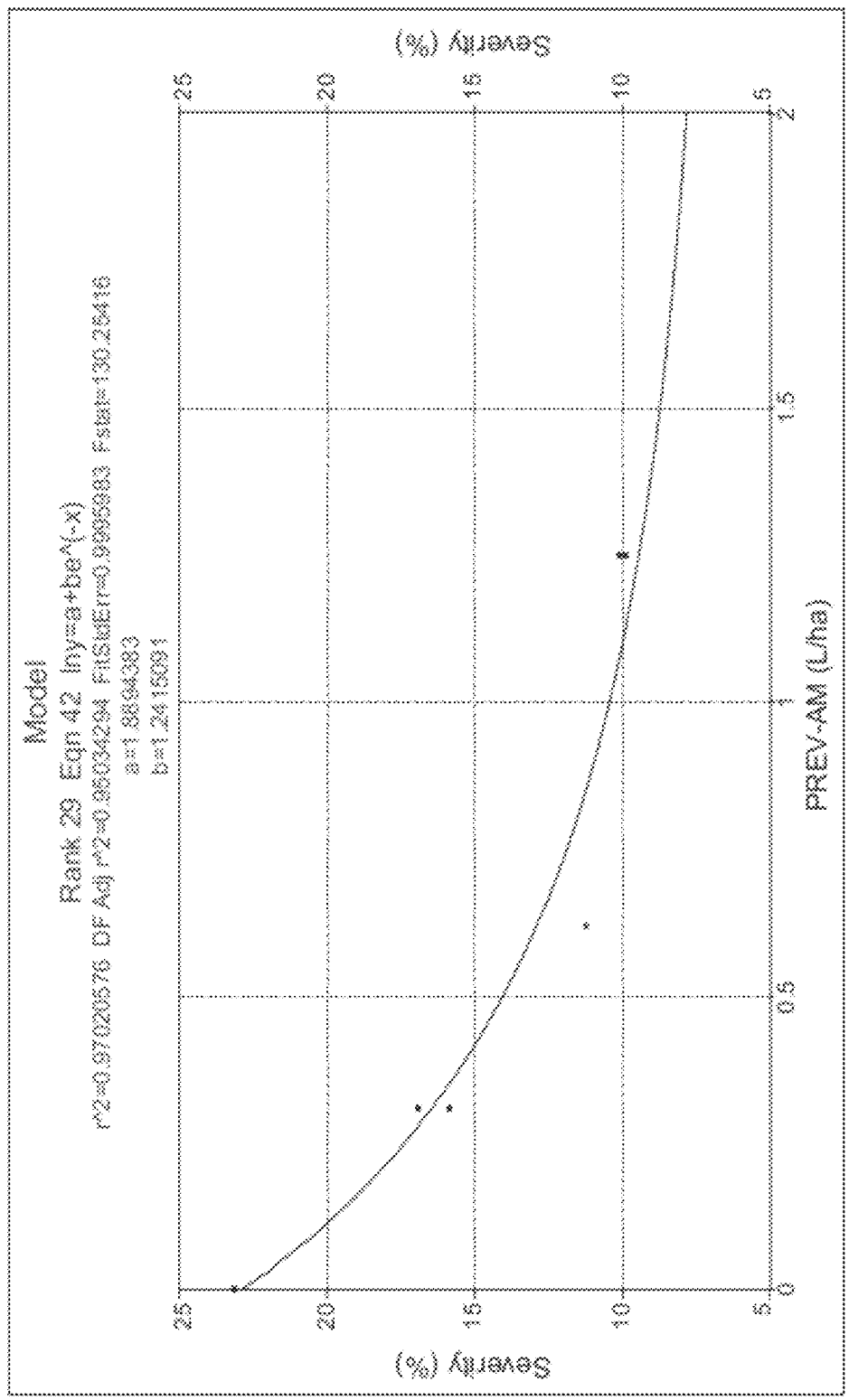
FIG. 1 shows dosage response curve for the control of powdery mildew severity on Chardonnay leaves after 9 sprays.

As used herein the term "pesticide" includes any substance that is intended for preventing, destroying, repelling or mitigating any pest. A pesticide may be a mixture of substances that prevents, destroys, repels, or mitigates any pest. The term pesticide includes "insecticide", "miticide", "fungicide", "herbicide", "acaricide", "miticide", and any agent used primarily for the control of insects and/or mites or fungi by preventing, destroying, repelling or mitigating any pests including insects, mites, and fungi which may be present in any environment whatsoever. As an example, the term "pesticide" includes the concepts of "acaricide" (agent used primarily in the control of plant-feeding mites, especially spider mites), and "insect pheromone" (agent used primarily for the control of behavioral responses of insects).

"Micro-droplets" as used herein are extra fine, very fine, and/or medium droplets having a particle size measured according to ASABE S-572 Droplet Standard. (ASABE: American Society of Agricultural and Biological Engineers)

As used herein, the terms "pesticidal effect" and "pesticidal activity" mean any direct or indirect action on the target pest that results in reduced feeding damage on any part of the plant, including but not limited to the seeds, roots, shoots and foliage of plants as compared to untreated plants. The term "insecticidal activity" has the same meaning as the term "pesticidal activity" except it is limited to those instances where the pest is an insect.

The terms "active against a (first or second) pest" include direct or indirect effects, such as inducing death of the pest, repelling the pest from any part of the plant, including but not limited to seeds, roots, shoots and/or foliage, inhibiting feeding of the pest on, or the laying of its eggs on, the plant seeds, roots, shoots and/or foliage, and inhibiting or preventing reproduction of the pest.

"Plant pest" means any organism known to associate with plants and which, as a result of that association, causes a detrimental effect on the plant's health and vigor. Plant pests include but are not limited to fungi, bacteria, insects, and mites or any other organism that causes a detrimental effect on the plant's health or vigor, excluding mammals, fish and birds.

The term "plant" as used herein encompasses whole plants and parts of plants such as roots, shoots, stems, leaves, flowers, seedlings, germinated seeds and seed, as well as cells and tissues within the plants or plant parts. The term "plant" also includes but not limited to trees, fruits, vegetables, flowering plants, herbs, bushes, vines, grasses, vines, mosses, and ferns.

As used herein, the "shoots and foliage" of a plant are to be understood to be the shoots, stems, branches, leaves and other appendages of the stems and branches of the plant after the seed has sprouted, including the roots of the plant. The shoots and foliage of a plant be understood to be those parts of the plant that have grown from the seed and/or shoots of a "mother" plant.

As used herein, the "region of the seed" is to be understood to be that region within about one inch of the seed.

The one or more high terpene (50% by weight or more) based oils, such as, but not limited to, citrus oil compositions of the present invention can be in the form of a liquid; suspension; emulsion; emulsion concentrate; slurry of particles in an aqueous medium (e.g., water). The concentration of the active ingredients in the formulation may be about 0.5% to about 35% by weight (w/w), or about 5-30%.

As used herein, the terms "terpene" or "high terpene" refer to any of a class of chemical compounds that are widespread in nature, mainly in plants as constituents of essential oils. Many terpenes are hydrocarbons, but oxygen-containing compounds such as alcohols, aldehydes or ketones (terpenoids) are also found. Their building block is the hydrocarbon isoprene, $CH_2=C(CH_3)-CH=CH_2$. Certain terpene hydrocarbons have molecular formulas $(C_5H_8)_n$, and may be classified according to the number of isoprene units. When terpenes are modified chemically, such as by oxidation or rearrangement of the carbon skeleton, the resulting compounds are generally referred to as "terpenoids." As used herein, the term "terpene" includes all "terpenoids." Examples of monoterpenes are: pinene, nerol, citral, camphor, menthol, limonene. Examples of sesquiterpenes are: nerolidol, farnesol. Examples of diterpenes are: phytol, vitamin $A_1$. Squalene is an example of a triterpene, and carotene (provitamin $A_1$) is a tetraterpene.

The one or more high terpene (50% by weight or more) based oils, which may be but are not limited to citrus oil compositions, of the invention may comprise from about 0.5% to about 35%, or about 1% to about 30% one or more high terpene (50% by weight or more) based oils such as but not limited to citrus oil by weight. In certain embodiments, the one or more high terpene (50% by weight or more) based oils such as but not limited to citrus oil compositions of the invention may comprise about 5% to about 20%, or about 12% to about 20% or about 12% to about 18% or about 12.7% citrus oil by weight.

The one or more high terpene (50% by weight or more) based oils, which may be but are not limited to citrus oil, compositions may comprise about 0.5% to about 35% by weight surfactant. When used as an adjuvant, the final surfactant concentration in the spray mixture may be about 0.05% to about 10%.

The one or more high terpene (50% by weight or more) based oils, which may be but are not limited to citrus oil, compositions may comprise about 0.5% to about 5% salt of boric acid by weight. In certain embodiments, the one or more high terpene (50% by weight or more) based oils such as but not limited to citrus oil compositions of the invention may comprise about 2.1% salt of boric acid by weight.

In certain embodiments, the one or more high terpene (50% by weight or more) based oils such as but not limited to citrus oil compositions of the invention may further comprise one or more insecticides, fungicides, miticides, herbicides, nutrients and/or fertilizers. In these embodiments, the one or more high terpene (50% by weight or more) based oils such as but not limited to citrus oil compositions of the invention may comprise about 0.5% to about 35% insecticides, fungicides, miticides, herbicides, nutrients and/or fertilizers by weight. In certain embodiments, the one or more high terpene (50% by weight or more) based oils such as but not limited to citrus oil compositions of the invention may comprise about 35% insecticides, fungicides, miticides, herbicides, nutrients and/or fertilizers by weight.

In certain embodiments, one or more high terpene (50% by weight or more) based oils such as but not limited to citrus oil compositions contemplated herein, the pH of the composition is between about 4.0 to about 9.0, about 6.0 to about 9.0, or about 7.8 to about 8.0.

The active mixture of the present invention can be in the form of a liquid; suspension; emulsion; emulsifiable concentrate or slurry of particles in an aqueous medium The pesticide composition of the present invention to be applied in a spray mixture of micro-droplets can be made of an active mixture, which is in the form of said liquids, emulsifiable concentrates or suspensions. The emulsifiable concentrates or emulsions of the active mixture may be prepared by dissolving the active mixture in an organic solvent optionally containing a wetting or emulsifying agent and then adding the dissolved product to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Such liquids, emulsifiable concentrates and suspension concentrates will normally contain surfactants known in the art, e.g. a wetting agent, dispersing agent, emulsifying agent or suspending agent. These agents can be cationic, anionic or nonionic agents.

The active mixtures of the invention may comprise from 0.5 wt % to 35% wt %, preferably 1 wt % to 30 wt % high terpene containing oils such as but not limited to citrus oil. In a preferred embodiment, the active mixtures of the invention may comprise 2 wt % to 20 wt %, preferably 12 wt % to 20 wt %, more preferably 12 wt % to 18 wt % and most preferably 15 wt % citrus oil.

When used as a pesticide the active mixtures of the present invention may comprise 0.5 wt % to 35 wt % surfactant. In a second embodiment, when used as an adjuvant, the final surfactant concentration in the spray mix may be 0.05 wt % to 10 wt % or may be between 0.025 wt % to 0.05 wt %. If not mentioned otherwise all number ranges and preferred substances can be hold for both embodiments, i.e. for the pesticide and the adjuvant.

The active mixtures of the invention may comprise 0.5 wt % to 5 wt % boric acid. In a preferred embodiment the active mixture comprises 2.1 wt % boric acid.

The active mixtures of the invention may further comprise one or more insecticides, fungicides, miticides, herbicides, nutrients and/or fertilizers. Preferably, the active mixture of the invention comprises 0.5 wt % to 65 wt % insecticides, fungicides, miticides, herbicides, nutrients and/or fertilizers. In a preferred embodiment, the active mixture of the invention may comprise 20 wt % insecticides, fungicides, miticides, herbicides, nutrients and/or fertilizers.

Other conventional inactive or inert ingredients can be incorporated into the active mixtures. Such inert ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 5105), lecithin (e.g., Yelkinol P), polymeric dispersants polyvinylpyrrolidone/vinyl acetate PVP/VA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like.

Further inert ingredients useful in the present invention can be found in McCutcheon's, vol. 1, "Emulsifiers and Detergents," MC Publishing Company, Glen Rock, N.J., U.S.A., 1996. Additional inert ingredients useful in the present invention can be found in McCutcheon's, vol. 2, "Functional Materials," MC Publishing Company, Glen Rock, N.J., U.S.A., 1996.

The pesticide composition can be adapted to various applications and conditions by additives known in the art for improving the distribution, adhesive power and resistance to rain on surfaces treated with the pesticide composition. These compounds may be comprised in the active mixture. Preferably these compounds are limited to an amount of 2 wt % to 10 wt % with respect to the pesticide composition.

Methods of Application

Conventional spraying methods with low volumes result in the deposition of very fine droplets that dry quickly without run-off to the edges of leaves and fruit. During high volume sprays, droplets may be formed, and due to the nature of the pesticidal composition containing high concentration of surfactants, the surfactants repel each other and move towards the outer surface of the droplet. At this surface, the surfactants repel each other again with the result that they move towards the contact surface between the water and the plant tissue at which place they are concentrated and may cause phytotoxicity upon drying of the droplet. This phytotoxicity occurs as a ring at the edge of the droplet. In a large droplet, the volume of surfactant is large, and if they move towards the circumference of the droplet, the volume: circumference ratio is much larger than with a very fine droplet. In the latter case, there is less chance of a phytotoxic concentration accumulating at the circumference of a droplet. Fine droplets therefore spread the same amount of surfactants more evenly in lower concentrations over the plant surface whereas large droplets tend to lead to high concentrations in certain areas and lower concentrations in other areas. These high concentrations may lead to phytotoxic reactions, necessitating the initial limiting of the concentrations of product to safe levels.

The present invention is based in part on the finding that at lower volumes the efficacy of the product is related to the amount of product used per area and that in order to apply the amount in a low volume, the concentration must be increased. It conventional methods, when used at high volumes, the same concentration of product would result in severe phytotoxicity. In Example 2, it is shown that at low volumes it is not the concentration of product that is related to control of powdery mildew, but the amount that was applied. In FIG. 1 it is shown that the severity of powdery mildew depends on the amount of product sprayed, whether this amount is applied at a higher volume and lower concentration or lower volume and higher concentration. (Compare 1.25 L/ha of the orange oil pesticide applied at either 0.25% and 500 L/ha or 0.5% and 250 L/ha. Also compare 0.31 L/ha applied at either 0.125% and 250 L/ha or 0.75% and 125 L/ha.) Therefore when lower volumes are used, a higher concentration of the product is needed to apply the same amount. If the amount needed to obtain sufficient control in this trial is extrapolated to be 2 to 3 liter product, at 125 liter of spray volumes the concentration would be 1.6% v/v to 2.4%. This becomes even more pronounced at lower volumes. Table 5 (Example 3) shows the results of a spray trial conducted on citrus by means of a fogger at a rate of 42 L/ha. The adjuvant was applied at a concentration of 22.2% v/v alone or with other pesticides as indicated. The surprising finding was that this was not phytotoxic in spite of the high concentration of the product.

The concentration to use would depend on the amount of product to be sprayed, but could for example, in the case of 10 L/ha (liter/hectare) application could go as high as 25% (volume/volume). In one embodiment, the concentration of the pesticide is between about 2% to about 30% (volume/volume). In another embodiment, the volume of the pesticide is about 5 to about 200 L/ha (liters/hectare).

Pesticides applied to plants or crops in the manner described herein have reduced phytotoxic effect as compared to pesticides applied using conventional spraying or misting systems which delivers the pesticides as high volume sprays (200 to 10,000 L/ha.). These systems can put out 200 L on small crops to 10,000 L for large crops, like trees.

The methods of applying pesticides disclosed herein protect plants or crops against pests and have reduced phytotoxicity as compared to methods delivering pesticides in high volumes, such as conventional spraying systems of high volumes.

The present invention is based in part on the finding that applying pesticides at a high concentration in a low volume reduces the phytotoxicity effect of the pesticide. The present invention provides a method of applying a pesticidal composition at a high concentration in a low volume. The method of the present invention comprises forming micro-droplets of an insecticidal composition and applying the micro-droplets of the composition to a plant. The method of applying pesticides at a high concentration in a low volume of the present invention may have little, or no, phytotoxicity effect as compared to conventional methods of applying pesticides at a high concentration.

The micro-droplets of pesticides may also be formed using an electrostatic sprayer or a fogger, such as the London Fogger (see http://www.londonfogger.com or a Cima sprayer (see http://www.cima.it/ENGLISH/EN_Sprayers.htm). The micro-droplets may be about 60 to 280 microns, about 150 to 210 microns, or about 140 to 160 microns in size.

The micro-droplets of pesticidal compositions disclosed herein may be applied in a number of ways. For example, they can be applied directly to the foliage of a plant or to seeds.

The micro-droplets of pesticidal compositions may be applied using methods including but not limited to spraying, wetting, misting, fogging, dampening, drizzling, aerial crop dusting via airplane or helicopter.

Lower volume sprayers such as but not limited to electrostatic sprayers and foggers are able to supply fine mist sprays that provide very efficient coverage of the surface of plants. Volume may be as low as 10 L/ha and up to 200 L/ha. These spray methods provide very efficient "wrap-around" application of the sprayed material to the plant surface or onto any pest that is present.

Application can be to any part of the plant or seed including the foliage, stems, branches or roots, or to the seed before it is planted, or to paddy water or to hydroponic culture systems. The citrus oil compositions disclosed herein may be sprayed onto vegetation using electrodynamic spraying techniques or other low volume methods.

The pesticides may be applied as micro-droplets of emulsifiable concentrates or suspensions. Emulsifiable concentrates or emulsions may be prepared by dissolving the citrus oil composition in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

The micro-droplets of pesticidal composition may be applied as sprays in the form of aerosols wherein the formulation is held in a container under pressure of a propellant, e.g. fluorotrichloromethane or dichlorodifluoromethane.

The pesticidal composition may also include additives for improving the distribution, adhesive power and resistance to rain on treated surfaces, the citrus oil compositions can be better adapted for various utilities.

The present invention provides a method of reducing phytotoxic effects of a pesticide comprising applying the pesticide to a plant or crop at a high concentration and low volume, wherein the phytotoxic effect is reduced as compared to applying the pesticide at a low concentration and high volume. The pesticide may be applied at a volume of between 5 L/ha to 200 L/ha at a concentration of between about 0.2% to 30% v/v. The pesticide may be applied in the form of micro-droplets. The micro-droplets may be about 60 to 280 microns, about 150 to 210 microns, or about 140 to 160 microns in size. The pesticide may be applied to the plant or crop using an electrostatic sprayer or fogger.

Pesticidal Compositions

The method of the present invention provides for the delivery of various pesticidal compositions to plants at a high concentration in a low volume.

The pesticidal compositions may include high terpene based oil compositions. Examples of high terpene (50% by weight or more) based oils, include but are not limited to citrus oils, pine oils, and other naturally occurring oils of plants that contain 50% or more terpenes. Citrus oils include but are not limited to orange oil, lemon oil, lime oil, grapefruit oil and tangerine oil. Citrus oils may be obtained by any method from a citrus fruit. For example, citrus oil may be obtained from the skin or peel of a citrus fruit. Other methods of obtaining the citrus oil include but are not limited to cold pressing techniques.

The pesticidal compositions may also include surfactants. Examples of surfactants include but are not limited to nonionic surfactants, anionic surfactants, cationic surfactants, and amphoteric surfactants.

Nonionic surfactants include agents such as sorbitan monolaurate, sorbitan monopalmitate, sorbitan sesquioleate, sorbitan trioleate, polyoxyethylene sorbitan monolaurate, polyoxyethylene sorbitan monostearate, polyethylene glycol monooleate, polyethylene glycol alkylate, polyoxyethylene alkyl ether, polyglycol diether, lauroyl diethanolamide, fatty acid iso-propanolamide, maltitol hydroxy fatty acid ether, alkylated polysaccharide, alkyl glucoside, sugar ester, oleophilic glycerol monostearate, self-emulsifiable glycerol monostearate, polyglycerol monostearate, polyglycerol alkylate, sorbitan monooleate, polyethylene glycol monostearate, polyoxyethylene sorbitan monooleate, polyoxyethylene cetyl ether, polyoxyethylene sterol, polyoxyethylene polyoxyethylene bees wax, and polyoxyethylene hydrogenated castor oil; and the like.

The alkyl glucosides are a class of non-ionic surfactants, which includes long chain alkyl glucosides or polyglucosides, that are the condensation products of (a) a long chain alcohol containing from about 6 to about 22, and from about 8 to about 14 carbon atoms, with (b) glucose or a glucose-containing polymer. The alkyl glucosides have about 1 to about 6 glucose residues per molecule of alkyl glucoside. In one embodiment, a glucoside is decyl glucoside, which is the condensation product of decyl alcohol with a glucose polymer and is available commercially from Henkel Corporation of Hoboken, N.J. under the tradename, "Plantaren 2000," In another embodiment, the alkyl glucoside is AKZO-NOBEL AG 6210.

Anionic surfactants include agents such as sodium stearate, potassium palmitate, sodium cetyl sulfate, sodium lauryl phosphate, sodium polyoxyethylene lauryl sulfate, triethanolamine palmitate, polyoxyethylene sodium lauryl phosphate, and sodium N-acyl glutamate; and the like. Calfoam® ES-603 is an example of an anionic surfactant. It is a clear liquid sodium salt of alcohol ethoxy sulfate with a faint alcohol odor. This biodegradable surfactant is pourable and pumpable at ambient temperatures and functions as a flash foamer and foam stabilizer in aqueous systems.

Cationic surfactants include agents such as stearyl dimethylbenzyl ammonium chloride, stearyl trimethyl ammonium chloride, benzalkonium chloride, and laurylamine oxide; and the like.

Amphoteric surfactants such as alkylaminoethyl glycine chloride and lecithin; and the like.

The pesticidal composition may also include one or more salts of boric acid. Salts of boric acid used in the insecticidal composition of the present invention may include any of the alkali earth metal salts of boric acid with any amount of hydration.

Borax, also called sodium borate, or sodium tetraborate, or disodium tetraborate, is an important boron compound, a mineral, and a salt of boric acid. It is usually a white powder consisting of soft colorless crystals that dissolve easily in water. Borax is used in detergents and cosmetics, as an ingredient in enamel glazes, glass, pottery, and ceramics, to make buffer solutions in biochemistry, as a fire retardant, a flux in metallurgy, and as a precursor for sodium perborate monohydrate that is used in detergents, as well as for boric acid and other borates.

The term "borax" is used for a number of closely related minerals or chemical compounds that differ in their crystal water content, but usually refers to the decahydrate. Commercially sold borax is usually partially dehydrated. In embodiments of the invention, the decahydrate is used in the claimed compositions.

Borax occurs naturally in evaporate deposits produced by the repeated evaporation of seasonal lakes. The most commercially important deposits are found in Turkey and near Boron, Calif. and other locations in the American southwest, the Atacama Desert in Chile, and in Tibet. Borax can also be produced synthetically from other boron compounds.

The term borax is often used for a number of closely related minerals or chemical compounds that differ in their crystal water content: Anhydrous borax ($Na_2B_4O_7$); Borax pentahydrate ($Na_2B_4O_7.5H_2O$); Borax decahydrate ($Na_2B_4O_7.10H_2O$), Borax is generally described as $Na_2B_4O_7.10H_2O$. However, it may also be formulated as $Na_2[B_4O_5(OH)_4].8H_2O$, since borax contains the $[B_4O_5(OH)_4]^{2-}$ ion. In this structure, there are two four-coordinate boron atoms (two $BO_4$ tetrahedra) and two three-coordinate boron atoms (two $BO_3$ triangles). Borax is also easily converted to boric acid and other borates. If left exposed to dry air, it slowly loses its water of hydration and becomes the white and chalky mineral tincalconite ($Na_2B_4O_7.5H_2O$).

An example of a high terpene based oil pesticidal composition is an orange oil pesticide. The said orange oil pesticide includes water, sulfonic acid, caustic soda, urea, sodium laureth sulfate (60%), non-ionic linear alcohol ethoxylate, sodium $C_{14-16}$ olefin sulfonate, orange, methyl paraben, butylated hydroxytoluene, sodium tetraborate decahydrate, and propyl paraben.

The high terpene based oil compositions used in the present invention may also include one or more other agents. For example, the agent may be an insecticide, a fungicide, an herbicide, a miticide, an acaricide, an insect pheromone, or a combination thereof. The agent may be an adjuvant to enhance the activity of the pesticide or other crop protection chemicals. The agent may be a fertilizer or a nutrient such as nitrogen-, potassium- or phosphorus-containing fertilizers.

Furthermore, the high terpene oil may be used as an adjuvant. The absorption of any associated product may be increased by increasing the concentration of the adjuvant. The high terpene based oil compositions comprising orange oil may increase the penetrability of the cuticle of the plant surface by opening up minute pores, allowing other substances to penetrate. The same applies to soft bodied insects where the protective layer is disrupted, allowing pesticidal products to penetrate into the living tissues underneath.

Seaweed extracts may be used as fertilizers. Seaweed is a loose colloquial term encompassing macroscopic, multi-cellular, benthic marine algae. The term includes some members of the red, brown and green algae. Seaweed may belong to one of several groups of multi-cellular algae: the red algae, green algae, and brown algae. As these three groups are not thought to have a common multi-cellular ancestor, the seaweeds are a paraphyletic group. In addition, some tuft-forming blue-green algae (Cyanobacteria) are sometimes considered as seaweeds.

Macronutrients required by plants can be divided into two groups, primary and secondary nutrients. The primary nutrients are nitrogen, phosphorus and potassium. Plants use large amounts of these nutrients for their growth and survival. The secondary nutrients are calcium, magnesium and sulfur.

There are at least eight micro-nutrients essential to plant growth and health that are only needed in very small quantities. These are manganese, boron, copper, iron, chlorine, cobalt, molybdenum, and zinc. Some also consider sulfur a micronutrient. Though these are present in only small quantities, they are all necessary.

Boron is believed to be involved in carbohydrate transport in plants; it also assists in metabolic regulation. Boron deficiency will often result in bud dieback. Boron is also essential for pollen tube growth in plants.

Chlorine is necessary for osmosis and ionic balance; it also plays a role in photosynthesis.

Cobalt is essential to plant health. Cobalt is thought to be an important catalyst in nitrogen fixation. It may need to be added to some soils before seeding legumes.

Copper is a component of some enzymes and of vitamin A. Symptoms of copper deficiency include browning of leaf tips and chlorosis.

Iron is essential for chlorophyll synthesis, which is why an iron deficiency results in chlorosis.

Manganese activates some important enzymes involved in chlorophyll formation. Manganese deficient plants will develop chlorosis between the veins of its leaves. The availability of manganese is partially dependent on soil pH.

Molybdenum is essential to plant health. Molybdenum is used by plants to reduce nitrates into usable forms. Some plants use it for nitrogen fixation, thus it may need to be added to some soils before seeding legumes.

Zinc participates in chlorophyll formation, and also activates many enzymes. Symptoms of zinc deficiency include chlorosis and stunted growth.

TABLE 1

List of minimum and maximum elemental contents in liquid fertilizers

| Ingredient | Ingredient Symbol | Minimum g/kg | Maximum g/kg | Minimum % w/w | Maximum % w/w |
| --- | --- | --- | --- | --- | --- |
| Nitrogen | N | 51 | 96 | 5.1 | 9.6 |
| Phosphorus | P | 10 | 63 | 1 | 6.3 |
| Potassium | K | 32 | 83 | 3.2 | 8.3 |
| Calcium | Ca | 56.6 | 195 | 5.66 | 19.5 |
| Magnesium | Mg | 9 | 55 | 0.9 | 5.5 |
| Boron | B | 0.2 | 115 | 0.02 | 11.5 |
| Iron | Fe | 1 | 70 | 0.1 | 7 |
| Manganese | Mn | 0.5 | 90 | 0.05 | 9 |
| Molybdenum | Mo | 0.005 | 0.28 | 0.0005 | 0.028 |

TABLE 1-continued

List of minimum and maximum elemental contents in liquid fertilizers

| Ingredient | Ingredient Symbol | Minimum g/kg | Maximum g/kg | Minimum % w/w | Maximum % w/w |
|---|---|---|---|---|---|
| Zinc | Zn | 0.5 | 120 | 0.05 | 12 |
| Copper | Cu | 0.5 | 140 | 0.05 | 14 |
| Sulphur | S | 10 | 12.4 | 1 | 1.24 |

The agent may be a plant growth regulator. Plant growth regulators, also known as plant hormones and phytohormones are chemicals that regulate plant growth. According to a standard animal definition, hormones are signal molecules produced at specific locations that occur in very low concentrations and cause altered processes in targeted cells at other locations. Plant hormones, on the other hand, are distinct from animal hormones, since they are often not transported to other parts of the plant and production is not limited to specific locations. Plants lack tissues or organs specifically for the production of hormones; unlike animals, plants tack glands that produce and secrete hormones that are then circulated around the body. Plant hormones shape the plant, affecting seed growth, time of flowering, the sex of flowers, senescence of leaves and fruits, they affect which tissues grow upward and which grow downward, leaf formation and stem growth, fruit development and ripening, plant longevity and plant death.

The pesticides used in the methods of the present invention may comprise one or more high terpene containing oils. The high terpene containing oil may be a citrus oil selected from the group containing orange oil, lemon oil, lime oil, grapefruit oil, and tangerine oil. The pesticide may comprise one or more high terpene containing oils and one or more surfactants. The surfactants may be selected from the group consisting of nonionic surfactants, anionic surfactants, cationic surfactants, and amphoteric surfactants.

In addition to the high terpene oils and surfactants, the pesticides of the present invention may further comprise borax, a fertilizer, a micro-nutrient, an insecticide, a fungicide, an herbicide, an acaricide, or a combination thereof. The pesticides of the present invention may also include propylene glycol, sodium laureth sulfate, secondary alcohol ethoxylate, urea, ethylenediaminetetra acetic acid, methyl paraben, ethanol, and a combination thereof.

Plant Varieties and Crops

The methods of the present invention may be used for agricultural and horticultural purposes. The methods described herein may be used to protect plants and crops including their seeds, roots, and/or the above-ground parts of field, forage, plantation, glasshouse, orchard or vineyard crops, grasses, turf, ornamentals, plantation, household or forest trees, against pests. The methods described herein have reduced phytotoxic effect as compared to delivering pesticides in high volumes such as conventional methods of spraying and misting.

The plants or crops that may be treated using the methods disclosed herein can be any species of plant or crop. The plant or crop species may be those that are agronomically or horticulturally important. In particular, the plant species may be corn, peanut, canola/rapeseed, soybean, curcubits, crucifers, cotton, beets, rice, sorghum, sugar beet, wheat, barley, rye, sunflower, tomato, sugarcane, tobacco, oats, as well as other vegetable and leaf crops. In certain embodiments, the crops or plant species may include vineyards, citrus, pecans, almonds, all stone fruits, apples, pears, bananas, lawns, turf, home and garden varieties of plants.

The plants may also be any ornamental plants, including but not limited to rose, tulip, violet, daffodil, gladiolus, lavender, lilies, narcissus, orchid, hyacinth, chrysanthemum, crocus, iris, peonies, zephyranthes, carnation, anthurium, gloxinia, azalea, poinsettia, ageratum, bamboo, begonia, camellia, dahlia, dianthus, geranium, impatiens, lilies of the valley and lobelia.

In one embodiment of the invention, the plant or crop is a non-transgenic plant or crop.

In another embodiment of the invention, the plant or seed is a transgenic plant or seed from which a transgenic plant can grow. The transgenic plants and seeds may be engineered to express a desirable characteristic and, in particular, to have at least one heterologous gene encoding for the expression of a protein that has pesticidal activity and, in particular, has insecticidal activity. The heterologous gene in the transgenic plant or seed of the present invention can be derived from a microorganism such as *Bacillus, Rhizobiuin, Pseudomonas, Serratia, Trichoderma, Clavibacter, Glomus, Gliocladium* and *mycorrhizal fungi*. In particular, the present methods are especially beneficial when the heterologous gene is one that is derived from a *Bacillus* microorganism and the protein is active against corn rootworm.

The present methods are especially beneficial when the heterologous gene is one that is derived from a *Bacillus* microorganism and the protein is active against European corn borer. An example of a *Bacillus* microorganism is *Bacillus thuringiensis*. The heterologous gene may encode a modified Cry3Bh delta-endotoxin derived from *Bacillus thuringiensis*.

Target Pests

The methods of delivering pesticides described herein have reduced phytotoxic effect on plants and crops and at the same time protect plants and crops from pests. The methods of the present invention target pests that are adults or larvae of any pests or pests that feed on the seed, roots and/or shoots and foliage of the plant that is to be protected by the present methods.

Without further description, it is believed that one of ordinary skill in the art can, using the preceding description and the following illustrative examples, make and utilize the claimed invention. The following working examples therefore, specifically point out embodiments of the present invention, and are not to be construed as limiting in any way the remainder of the disclosure.

EXAMPLES

Example 1

Pesticidal Composition

An orange oil composition, referred to herein as the "orange oil pesticide," is prepared using the following ingredients.

TABLE 2

| | Chemical name | Nominal Concentration: |
|---|---|---|
| WATER | Water | 62.4% |
| BioSoft S-100 | Sulfonic Acid (Benzenesulfonicacid, dodecyl-) | 10.59% |

TABLE 2-continued

| | Chemical name | Nominal Concentration: |
|---|---|---|
| NaOH | Caustic soda (Sodium hydroxide (NaOH),) | 1.37% |
| Urea | Urea | 0.89% |
| Steol CS-460 | SODIUM LAURETH SULFATE (60%) | 7.13% |
| Tomadol/Serdox 1-7 or 9 | Non ionic Linear Alcohol Ethoxylate | 8.448% |
| Bio-Terge AS-40 | Sodium C14-16 Olefin Sulfonate | 1.78% |
| Orange Oil | Cold pressed orange oil | 6.00% |
| Methylparaben (Nipagin M) | Methyl Paraben | 0.20% |
| BHT | Butylated hydroxytoluene | 0.10% |
| US Borax | Sodium tetraborate decahydrate | 0.99% |
| Propylparaben | Propyl Paraben | 0.10% |
| Color FD & C Blue | | 0.001 |
| Yellow | | 0.001 |
| Citric Acid | | as needed for pH spec. |
| TOTAL WEIGHT. | | 100.00% |

If the composition is used as an insecticide, fungicide or miticide, the composition is diluted in water and used at a concentration of between about 0.025% up to about 30%.

If the composition is used with other insecticides, fungicides, miticides, herbicides, nutrients or fertilizers, the composition may be combined at a rate of between about 0.01% up to about 30% in tank mixes with insecticides, fungicides, miticides, herbicides, fertilizers and nutrients.

Example 2

Efficacy of Orange Oil Pesticide on Powdery Mildew at Various Concentrations and Volumes In this example, the efficacy of the orange oil pesticide at various concentrations and spray volumes against powdery mildew (*Uncinula necator*) on Chardonnay grapes was evaluated. The trial was specifically designed to test lower volume applications with an effective sprayer and to compare the effect of volume and concentration where the same amount of product per hectare (ha) was applied.

Wine grapes, cv. Chardonnay, in Somerset West, Western Cape, South Africa were treated with the orange oil pesticide to protect against powdery mildew as described below. Examples of orange oil pesticide that could typically be used, include, but are not limited to PREV-B2™, PREV-AM™ or BORIGAN™.

Statistical layout: Randomized Block layout with 6 treatments replicated in each of 4 blocks. Each experimental plot consisted of 14 vines with 7 or more vines on each side to serve as guard vines. Each experimental plot had 2 guard rows on both sides resulting in 4 guard rows being present between experimental plots.

Application equipment: The orange oil pesticide was applied to the grape vines with a tractor mounted Cima sprayer.

Treatment Schedule: The orange oil pesticide was applied to the grape vines according to the treatment schedule in Table 3.

TABLE 3

| | Treatments | |
|---|---|---|
| No. | Treatment | L/ha of orange oil pesticide |
| 1 | 0.25% X 125 L/ha | 0.31 |
| 2 | 0.25% X 250 L/ha | 0.62 |
| 3 | Untreated Control (UTC) | 0 |
| 4 | 0.25% X 500 L/ha | 1.25 |
| 5 | 0.5% X 250 L/ha | 1.25 |
| 6 | 0.125% X 250 L/ha | 0.31 |

The grapes were sprayed about every 10 days for about four months at the concentrations and volumes indicated in Table 3. An UTC as reference received no sprays at all.

Post Spray Assessment: The powdery mildew infection on 40 leaves per experimental plot was expressed as percentage of leaf area affected on the top of the leaves. Very little powdery mildew occurred on the dusters and no evaluation was made.

Statistical analysis: The means of the numbers for each value obtained were subjected to an analysis of variance and the treatment means were compared using Student's t-LSD at a 5% significance level with SAS version 8.2.

From the results it was clear that there was no statistical significant difference between treatments where the same volume, or amount, of orange oil pesticide was sprayed. Curves were fitted to the data based on volume to find the best fit for a dosage response curve. The best-fitting curve that had a 97% correlation with the amount of orange oil pesticide per hectare is presented under Results.

Results: The results are presented in Table 4 and FIG. 1.

TABLE 4

Powdery mildew severity for different treatments go Chardonnay leaves after 9 sprays.

| No. | Treatment | L/ha orange oil pesticide | % leaf area affected | Stats | |
|---|---|---|---|---|---|
| 3 | UTC | 0 | 23.18 | A | |
| 6 | 0.125% X 250 L/ha | 0.31 | 16.93 | B | Means followed by a common letter |
| 1 | 0.25% X 125 L/ha | 0.31 | 15.88 | B | do not differ significantly at P = 0.05 |
| 2 | 0.25% X 250 L/ha | 0.62 | 11.25 | C | |
| 4 | 0.25% X 500 L/ha | 1.25 | 9.90 | D | Means followed by a common letter |
| 5 | 0.5% X 250 L/ha | 1.25 | 10.10 | D | do not differ significantly at P = 0.05 |

All values at different amounts of the orange oil pesticide were statistically different from each other as indicated in Table 4. Where the same amounts were used but at different volumes and concentrations, the differences were not significant. Statistical data from the curve in FIG. 1 also indicated that the infection differed significantly between all amounts (L/ha) applied as well as the UTC.

Considering that the spraying intervals were longer than would normally be the case, the control obtained by the application of 1.25 L/ha was good and had the spray intervals been as planned, would have been sufficient for control of powdery mildew under the climatic conditions. From the extrapolation of the graph it is however clear that 2 to 3 L/ha would have provided better control. Considering that the disease pressure in this location is generally low, in the event of higher disease pressure, 2 to 3 L/ha may be used.

Conclusions: In this trial, it was shown that at low volumes it is not the concentration of product that is related to control of powdery mildew, but the amount that was applied. It can be concluded that within the parameters of the volumes and concentrations applied in the trial, the powdery mildew control obtained is best correlated with the amount of product applied. Provided an efficient sprayer is used, the same amount per hectare may be sprayed at lower or higher volume with a corresponding higher or lower concentration.

The efficacy of the orange oil pesticide is related to the amount of product used and not to the concentration as previously expected and disclosed.

Example 3

Dyna Fog Low Volume Spray with Different Pesticides

In this Example, different pesticides were sprayed with Dyna Fog low volume sprayer and evaluated. All treatments were applied using 9.34 L of adjuvant in 42 L/ha spray volume. Pretreatment count was taken a day prior to the application of the treatment. Application rates and treatment results are presented in Table 5 below. Examples of adjuvant that may be used include, but are not limited to WETCIT™, POLICIT™, CITRI-KING™ or the like.

the first 2 weeks after application. Starting from the $3^{rd}$ week post treatment, ACP started to re-infest the treated plots. But despite this re-infestation, lower ACP numbers were still observed in some treatments compared to the untreated control.

Example 4

Water Rate and Runoff

In this Example, low volume sprays of pesticides were applied to grape leaves to illustrate coverage. Application of tow volume sprays with adjuvant and fluorescent dye to illustrate the coverage obtained on a grape leaf. The dye reflects the ultra violet light beam shone directly onto it and shows how evenly the product associated with it is applied.

Figure 2A:
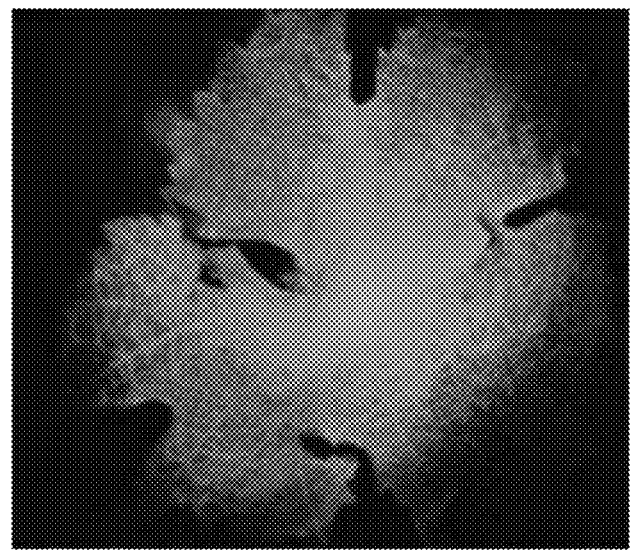
FIGS. 2A and 2B show coverage and runoff of product at specific liter per hectare (L/ha) water rate.
Figure 2B:
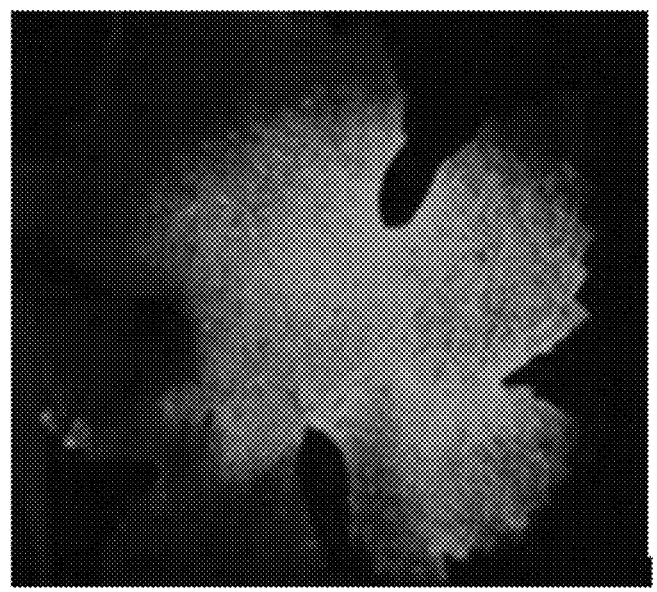

FIG. 2A shows product at 234 L/ha water rate. FIG. 2B shows product at 140 L/ha water rate. Product at 140 L/ha water rate showed excellent coverage on top and bottom of leaf even at lower water rates with less runoff and still no phytotoxic effect even at higher concentration rates (same rates per hectare in lower water volumes).

It should be understood that the foregoing discussion and examples merely present a detailed description of certain embodiments. It therefore should be apparent to those of ordinary skill in the art that various modifications and equivalents can be made without departing from the spirit and scope of the invention. All articles, publications, patents and documents referred to throughout this application are hereby incorporated by reference in their entirety.

TABLE 5

The Spraying of different pesticides using a Dyna Fog

| Treatment | Rate/ Hectare | Pre-Count | | 11 days post treatment | | 20 days post treatment | | 26 days post treatment | |
|---|---|---|---|---|---|---|---|---|---|
| | | Eggs/ flush | Nymphs/ Flush | Eggs/ flush | Nymphs/ Flush | Eggs/ Flush | Nymphs/ flush | Eggs/ Flush | Nymphs/ flush |
| Danitol + adjuvant | 1.4 kg 9.34 liters | 1.1 | 0.06 | 0.13b | 0b | 4.6b | 0.3b | 0a | 9.1ab |
| Agrimek + Adjuvant | 1.4 kg 9.34 liters | 1.1 | 0.06 | 1.51b | 0b | 3.3b | 1.3ab | 2.2a | 11.7a |
| Malathion + Adjuvant | 2.24 kg 9.34 liters | 1.1 | 0.06 | 0b | 0b | 8.6ab | 1.6ab | 1.7a | 5.2bc |
| Baythroid XL + Adjuvant | 168 g 9.34 liters 9.34 liters | 1.1 | 0.06 | 0b | 0.7b | 2.7b | 0.9ab | 1.3a | 1.8c |
| Micromite + Adjuvant | 437 g 9.34 liters | 1.1 | 0.06 | 0.9b | 0b | 2.2b | 0.7ab | 0.8a | 4.5bc |
| Dimethoate + Adjuvant | 2.24 kg 9.34 liters | 1.1 | 0.06 | 0.13b | 0b | 0.7b | 1.3ab | 0.2a | 0.6c |
| Lorsban + Adjuvant | 1.4 kg 9.34 liters | 1.1 | 0.06 | 0b | 0b | 5.5b | 5.2a | 0.4a | 0.4c |
| Adjuvant | 9.34 liters | 1.1 | 0.06 | 0.3b | 0.1b | 7.8ab | 3.8ab | 0.1a | 1.2c |
| Untreated control | | 1.1 | 0.06 | 6.2a | 1.8a | 12.8a | 3.8ab | 0.9a | 7.8ab |

Statistics:
a, b, c: Compare in the same column. Means followed by a common letter do not differ significantly at P = 0.05.

Conclusions: It can be concluded that all pesticides sprayed via the Dyna Fog at the rate of 42 L/ha (low volume) provided significant reductions of ACP nymphs and eggs for

What is claimed is:
1. A method of reducing a phytotoxic effect of a pesticide, comprising:

applying a spray mixture in an amount of 10 to 200 L/ha to a plant, wherein the spray mixture comprises the pesticide;

wherein the pesticide comprises:
(a) one or more surfactants in a concentration of 10% to 35%, based on a weight of the pesticide; and
(b) one or more high terpene containing oils in a concentration of 6% to 35%, based on the weight of the pesticide;

wherein a concentration of the pesticide is between 2% to 30%, based on a volume of the spray mixture; and wherein the spray mixture is applied in a form of micro-droplets having a volume median diameter of 60 μm to 280 μm, whereby a phytotoxic effect of applying the spray mixture comprising the pesticide to the plant is reduced.

2. The method of claim 1, wherein the spray mixture is applied to the plant via an electrostatic sprayer.

3. The method of claim 1, wherein the spray mixture is applied as micro-droplets in a size selected from the group consisting of about 130 to 210 microns, about 150 to 210 microns, and about 140 to 210 microns.

4. The method of claim 1, wherein the spray mixture is applied to the plant using a fogger.

5. The method of claim 1, wherein the pesticide comprises one or more surfactants selected from the group consisting of nonionic surfactants, anionic surfactants, cationic surfactants, and amphoteric surfactants.

6. The method of claim 1, wherein the one or more high terpene containing oils is a citrus oil.

7. The method of claim 1, wherein the one or more high terpene containing oils contain at least 50 percent terpene and is a citrus oil.

8. The method of claim 6, wherein the citrus oil is selected from the group consisting of orange oil, lemon oil, lime oil, grapefruit oil and tangerine oil.

9. The method of claim 1, wherein the pesticide further includes borax.

10. The method of claim 1, wherein the pesticide further comprises a fertilizer.

11. The method of claim 1, wherein the pesticide further comprises micro-nutrients.

12. The method of claim 1, wherein the pesticide further comprises an insecticide, fungicide, herbicide or acaricide.

13. A method of reducing a phytotoxic effect of a pesticide, comprising:

applying a spray mixture in an amount of 500 L/ha to a plant, wherein the spray mixture comprises the pesticide;

wherein the pesticide comprises:
(a) one or more surfactants in a concentration of 10% to 35%, based on a weight of the pesticide; and
(b) one or more high terpene containing oils in a concentration of 6% to 35%, based on the weight of the pesticide;

wherein a concentration of the pesticide is between 2% to 30%, based on a volume of the spray mixture; and wherein the spray mixture is applied in a form of micro-droplets having a volume median diameter of 60 μm to 280 μm, whereby a phytotoxic effect of applying the spray mixture comprising the pesticide to the plant is reduced.

14. The method of claim 13, wherein the spray mixture is applied to the plant via an electrostatic sprayer.

15. The method of claim 13, wherein the spray mixture is applied as micro-droplets in a size selected from the group consisting of about 130 to 210 microns, about 150 to 210 microns, and about 140 to 210 microns.

16. The method of claim 13, wherein the spray mixture is applied to the plant using a fogger.

17. The method of claim 13, wherein the pesticide comprises one or more surfactants selected from the group consisting of nonionic surfactants, anionic surfactants, cationic surfactants, and amphoteric surfactants.

18. The method of claim 13, wherein the one or more high terpene containing oils is a citrus oil.

19. The method of claim 13, wherein the one or more high terpene containing oils contain at least 50 percent terpene and is a citrus oil.

20. The method of claim 19, wherein the citrus oil is selected from the group consisting of orange oil, lemon oil, lime oil, grapefruit oil and tangerine oil.

21. The method of claim 13, wherein the pesticide further includes borax.

22. The method of claim 13, wherein the pesticide further comprises a fertilizer.

23. The method of claim 13, wherein the pesticide further comprises micro-nutrients.

24. The method of claim 13, wherein the pesticide further comprises an insecticide, fungicide, herbicide or acaricide.

* * * * *